United States Patent
Geiger et al.

(10) Patent No.: US 7,070,328 B2
(45) Date of Patent: Jul. 4, 2006

(54) METHOD FOR THE COMPENSATION OF IMAGE DISTURBANCES IN THE COURSE OF RADIATION IMAGE RECORDINGS AND RADIATION IMAGE RECORDING APPARATUS

(75) Inventors: Bernhard Geiger, Buckenhof (DE); Sigrid Joite-Barfuss, Erlangen (DE); Claudius Molz, Buckenhof (DE); Gudrun Roth-Ganter, Moessingen-Oeschingen (DE)

(73) Assignee: Siemens Aktiengesellschaft, Munich (DE)

( * ) Notice: Subject to any disclaimer, the term of this patent is extended or adjusted under 35 U.S.C. 154(b) by 209 days.

(21) Appl. No.: 10/803,998

(22) Filed: Mar. 19, 2004

(65) Prior Publication Data

US 2004/0223590 A1  Nov. 11, 2004

(30) Foreign Application Priority Data

Mar. 20, 2003  (DE) ............................... 103 12 450

(51) Int. Cl.
*G21K 1/02* (2006.01)

(52) U.S. Cl. .................... 378/207; 378/154; 250/505.1

(58) Field of Classification Search ................. 378/62, 378/98.7, 98.8, 147, 149, 150, 151, 154, 378/155, 205, 207; 250/370.09, 505.1
See application file for complete search history.

(56) References Cited

U.S. PATENT DOCUMENTS

| | | | |
|---|---|---|---|
| 4,081,687 A * | 3/1978 | York et al. | 378/149 |
| 4,466,113 A * | 8/1984 | Strecker | 378/149 |
| 5,050,198 A * | 9/1991 | Honda | 378/98.2 |
| 5,198,680 A * | 3/1993 | Kurakake | 250/505.1 |
| 5,434,902 A * | 7/1995 | Bruijns | 378/98.7 |
| 5,974,113 A * | 10/1999 | Bruijns et al. | 378/98.7 |
| 6,246,746 B1 * | 6/2001 | Conrads et al. | 378/98.7 |
| 6,422,750 B1 * | 7/2002 | Kwasnick et al. | 378/205 |
| 6,502,984 B1 * | 1/2003 | Ogura et al. | 378/206 |
| 6,542,575 B1 * | 4/2003 | Schubert et al. | 378/98.4 |
| 6,690,767 B1 * | 2/2004 | Davis | 378/154 |
| 6,795,529 B1 * | 9/2004 | Barnes et al. | 378/155 |
| 6,826,256 B1 * | 11/2004 | Inoue | 378/154 |
| 6,895,080 B1 * | 5/2005 | Baba et al. | 378/154 |

\* cited by examiner

*Primary Examiner*—Allen C. Ho
(74) *Attorney, Agent, or Firm*—Harness, Dickey & Pierce

(57) ABSTRACT

A method is for the compensation of image disturbances in the course of a radiation image recording caused by a defocusing of an antiscatter grid, arranged in the beam path between a beam source and a digital radiation image receiver and focused with respect to a specific distance from the focus of the beam source. Such image disturbances are caused by a defocusing-dictated attenuation of the primary radiation incident on the radiation image receiver. A solid-state image detector includes radiation-sensitive pixels arranged in matrix form and a device for pixelwise amplification of the radiation-dependent signals. In the method, at least some of the signals supplied in pixelwise fashion are amplified by an amplifying device in a manner dependent on the actual distance of the antiscatter grid from the focus.

30 Claims, 3 Drawing Sheets

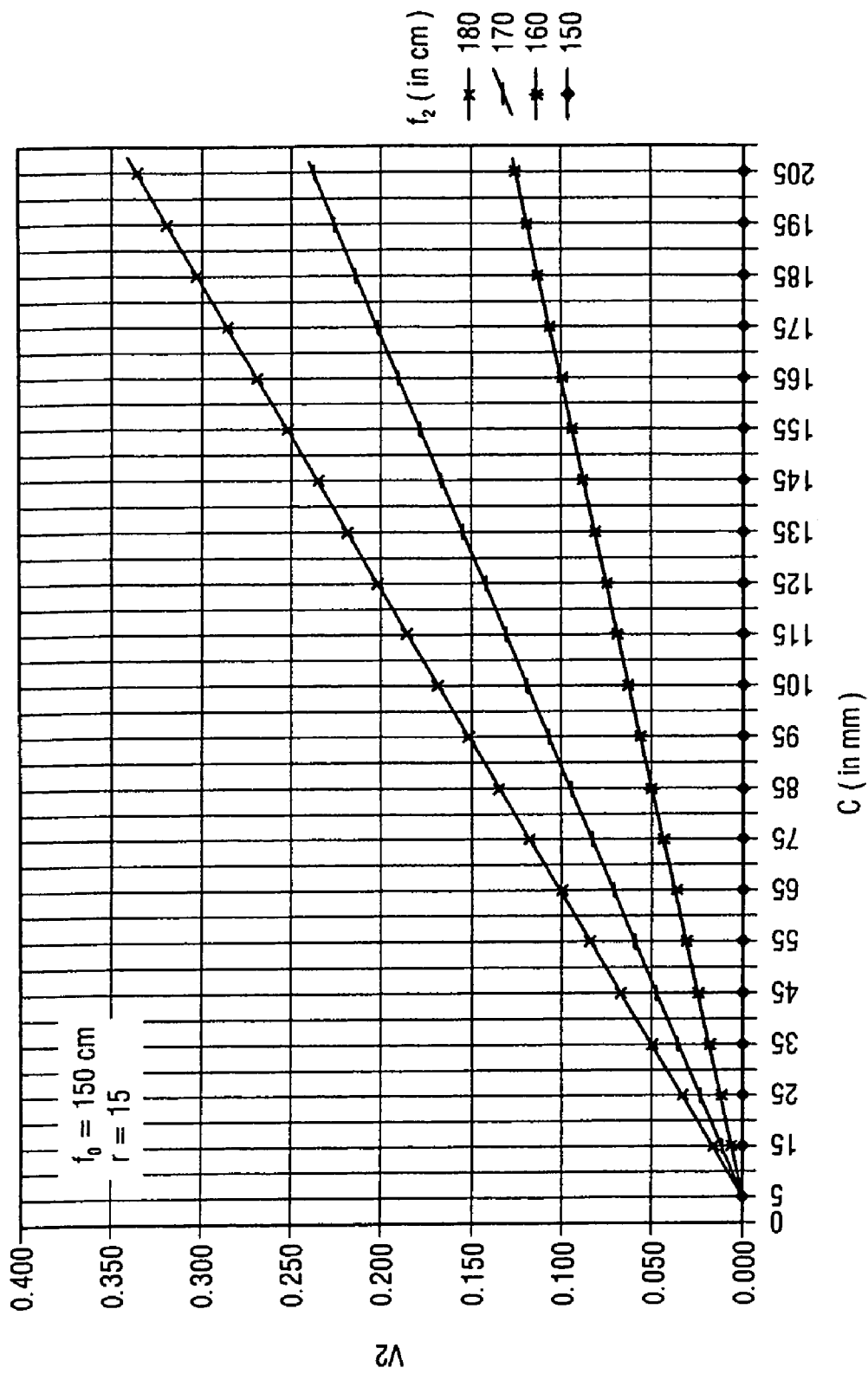

METHOD FOR THE COMPENSATION OF IMAGE DISTURBANCES IN THE COURSE OF RADIATION IMAGE RECORDINGS AND RADIATION IMAGE RECORDING APPARATUS

The present application hereby claims priority under 35 U.S.C. §119 on German patent application number DE 103 12 450.0 filed Mar. 20, 2003, the entire contents of which are hereby incorporated herein by reference.

FIELD OF THE INVENTION

The invention generally relates to a method for the compensation of image disturbances. Preferably, the disturbances are in the course of a radiation image recording caused by a defocusing of an antiscatter grid. The grid is preferably arranged in the beam path between a beam source and a digital radiation image receiver and is focused with respect to a specific distance from the focus of the beam source. The image disturbances are preferably caused by a defocusing-dictated attenuation of the primary radiation incident on the solid-state image detector. The radiation image receiver preferably has radiation-sensitive pixels arranged in matrix form and a device for pixelwise amplification of the radiation-dependent signals.

BACKGROUND OF THE INVENTION

The use of antiscatter grids in radiation, in particular X-ray, diagnosis is the most widely used and recognized method for reducing the proportion of scattered radiation in the imaging radiation, the primary radiation, and for improving the contrast of the radiation image recording. The grids that are mainly used nowadays are focused linear grids. These linear grids include absorber lamellae, generally lead lamellae, embedded in a carrier material, generally paper or plastic layers.

For focusing purposes, the absorber lamellae are arranged upright or inclined with respect to the vertical in such a way that the diverging primary radiation can pass through between the lamellae, but the scattered radiation is blocked (grid focusing). Each grid is focused with respect to a specific, defined distance from the focus of the beam source. The inclination of the absorber lamellae corresponds to the divergence of the primary beam cone at a specific distance with respect to which the grid is focused.

Any deviation from the focusing distance leads to a dose decrease in the primary radiation primarily in the image edge regions. This is due to the fact that, in the case of a deviation from the focusing distance, the clear width between the lamellae decreases and, consequently, more primary radiation is absorbed by way of the absorber lamellae, the absorption increasing with increasing deviation from the focusing distance, that is to say with increasing defocusing.

The distance tolerances which are specified for each grid and within which a defocusing still leads to acceptable, diagnostically meaningful images are based on a dose decrease of 40% at the image receiver edge as seen from the grid center (IEC/DIN 60627). In this case, the decrease is given not only by the different transmittivity of the grid in the case of nonfocusing, but also by the outwardly decreasing dose (square law of distance). The distance tolerance range used under these preconditions is primarily determined by the shaft ratio "R", that is to say the ratio of the width of the shaft between two lamellae to the height of the lamellae.

In the case of the digital radiation image receivers that are increasingly being used, e.g. in the form of solid-state detectors or flat detectors, use is made of antiscatter grids having a significantly higher number of lines (of e.g. 80 lines/cm) compared with the grids used e.g. in the case of film systems. In order to obtain the same selectivity (scattered radiation suppression) as in the case of the moving grids used in conventional film radiography (shaft ratio R=8 or 12), higher shaft ratios (e.g. R=15) are used in the case of grids having a high number of lines.

It is disadvantageous when using such grids in connection with digital image detectors, however, that the distance tolerance range, that is to say the range within which a defocusing which still leads to acceptable images may be given, is significantly limited compared with the e.g. moving grids with lower shaft ratios in customary film systems. This limited distance tolerance range demands a consistent changing of the grids in the event of a changing film-focus distance, that is to say the distance of the focus of the beam source from the solid-state image detector.

However, changing the grid is time-consuming and does not permit a continuous workflow in the context of examining patients. Furthermore, it is necessary to keep in each case different grids which are focused with respect to different film-focus distances, in order, by way of example, to be able to cover a customary distance range of 115 cm to 180 cm.

SUMMARY OF THE INVENTION

An embodiment of the invention is thus based on the problem of specifying a method and/or an apparatus which reduces or even eliminates at least one of the problems mentioned.

An embodiment of the invention provides for at least some of the signals supplied in pixelwise fashion to be amplified via the amplifying device in a manner dependent on the actual distance of the antiscatter grid from the focus.

The method according to an embodiment of the invention proposes electronically compensating for the disturbance component resulting solely from the defocusing, that is to say the defocusing-dictated dose attenuation, which is manifested in correspondingly weaker pixel signals. This can be done by amplifying at least some of the signals that are attenuated in disturbance-dictated fashion by use of the amplifying device assigned to a customary radiation detector. This makes it possible, depending on what is demanded and required, to be able to compensate for the defocusing-dictated disturbance by virtue of the fact that precisely the focusing-dictated weaker signals are elevated and, consequently, electronically adapted and compensated for.

This makes it possible to establish a noise which becomes somewhat stronger toward the edge of the solid-state image detector, but this is tolerable with regard to the technological gain in terms of information and work. It is thus ideally possible to be able to compensate for almost the entire defocusing-dictated signal attenuation by this device over the entire detector area or area of the pixel matrix. The compensation according to an embodiment of the invention acts in addition to the "flat field" correction which is customary in digital image detectors and is used to correct the dose attenuation resulting from the square law of distance toward the detector edge.

Thus, both the customary flat field correction and the defocusing-dictated correction can be achieved using the method according to an embodiment of the invention. As a result, it is possible to use one and the same grid, focused to a specific film-focus distance, over the entire routine work range (e.g. from 100 cm to 200 cm film-focus distance). Continuous work is thus possible; the manual change activities, which are laborious and interrupt the examination flow, are thus no longer incurred. Solid-state image detectors are discussed hereinafter, but any other type of digital radiation image receiver may be used instead of such an image detector.

According to a first refinement according to an embodiment of the invention, it may be provided that the pixel-related gain factors are determined computationally for the given actual distance of the antiscatter grid from the focus relative to the original focusing distance. The gain factors by which each individual pixel signal is amplified are thus calculated according to this refinement of an embodiment of the invention.

Parameters required for calculating the gain factors, such as grid-specific values (shaft ratio, focusing distance of the grid, the actual film-focus distance, the detector sensitivity, etc.), are available in solid-state image detector systems, so that it is possible to have recourse to the known formulae already revealed in the abovementioned specification IEC/DIN 60627. On the basis thereof, it is possible to determine the actual defocusing-dictated signal attenuation profile with respect to a given actual distance of the grid from the focus and thus to determine the local pixel-related signal attenuation or the magnitude thereof. This in each case relative to an exposure without an examination object, that is to say if only the antiscatter grid is arranged in the beam path. On the basis of these local pixel gain factors, it is then possible to amplify each pixel signal of the actual radiation image recording of the examination object in accordance with the defocusing attenuation stemming solely from the antiscatter grid.

By contrast, an alternative to the computational determination of the gain factors provides for the pixelwise gain factors to be chosen from a table assigned to the actual distance of the antiscatter grid from the focus. In this refinement of an embodiment of the invention, a plurality of correction tables are stored in the amplifying device, the correction tables having been recorded for specific distances of a focused antiscatter grid from the focus. For the recording of the correction tables, only the antiscatter grid is situated at the respectively chosen distance that deviates from the focusing distance in the beam path. This yields a signal profile over the pixel matrix which reproduces the defocusing-dictated signal attenuation.

Corresponding pixel-related gain factors can then be determined therefrom and are combined in the final correction table. If the actual distance of the grid from the focus is then known, the correction table assigned to this actual distance or the correction table nearest to it (in the absence, with respect to the actual distance, of a correction table which was created in the case of precisely this distance) is chosen, and use is made of those gain factors from the table which are assigned to the pixel signals that are actually to be amplified.

In this case, the respective gain factor, as can be taken from the table, may be adapted computationally in the case of a difference between the actual distance and the distance on which the table is based. Since, as described, generally only a specific number of tables have been recorded with respect to specific distances, and the actual distance does not have to correspond to the distance on which the correction table is based, it is possible in this way to effect a computational adaptation, if appropriate by suitable interpolation between the values of two nearest distance-specific tables, etc.

In accordance with an expedient development of the concept of an embodiment of the invention, it may be provided that only the pixel signals of those pixels whose signals—relative to the defocusing-dictated signal attenuation exclusively of the antiscatter grid without a transillumination object situated in the beam path—lie below a predetermined threshold value are amplified.

As explained above, radiation images with a dose decrease of up to at most 40% are deemed still acceptable. If it then emerges that the actual defocusing of the antiscatter grid with respect to the chosen focus distance leads to a greater attenuation than the aforementioned 40% e.g. only in narrow pixel matrix regions at the opposite detector edges, it is also the case that in the context of the compensation, only the pixel signals of these signals which are attenuated to a greater extent than by 40% are amplified. In this case, the threshold value may define a defocusing-dictated attenuation of 40%, as provided in accordance with the specification, but also less, depending on the design.

A correspondingly expedient refinement of an embodiment of the invention furthermore provides for the signals to be amplified by the gain factors to a predetermined threshold value. This also makes use of the fact that still acceptable images are present in the case of a signal decrease of up to 40%. Pixel signals which are attenuated to a greater extent are now not elevated to 100%, but only for example to 60%, that is to say that effectively a signal decrease with respect to the elevated pixel of only a permissible 40% is present.

This leads on the one hand to an acceptable radiation image; on the other hand, the amplification-dictated noise is within fully acceptable limits. It goes without saying that it is possible also to choose other threshold values, e.g. 70% or 80%. It is expedient in this case if the threshold value (be it the one which defines the pixel signals which are to be elevated, or the threshold value which defines the gain limit) is adjustable, that is to say can thus be chosen during operation.

In addition to the method according to an embodiment of the invention, an embodiment of the invention furthermore relates to an apparatus for radiation image recording. In a particular embodiment, it relates to one suitable for carrying out the method.

The apparatus of one embodiment of the invention includes a beam source, a digital radiation image detector with radiation-sensitive pixels arranged in matrix form with an assigned device for the pixelwise amplification of the pixel signals, and an antiscatter grid, which is arranged between beam source and radiation image detector and is focused with respect to a specific distance from the focus of the beam source. This apparatus is distinguished, according to an embodiment of the invention, by the fact that the device is designed for the compensation of image disturbances caused by a defocusing of the antiscatter grid, which image disturbances are caused by a defocusing-dictated attenuation of the primary radiation incident on the radiation image detector, for the pixelwise amplification of at least some of the signals supplied in a manner dependent on the actual distance of the antiscatter grid from the focus.

In this case, the device may be designed for the computational determination of the pixel-related gain factors for the given actual distance of the antiscatter grid from the focus relative to the original focusing distance. This additional amplification is one in addition to the flat field correction which is to be performed in any case by the amplifying device and which serves to compensate for the attenuation governed by the square law of distance toward the edge.

As an alternative to the computational determination (or in addition thereto), one or a plurality of tables with pixel-specific gain factors, said tables being assigned to one or a plurality of specific distances of the antiscatter grid from the focus, may be stored in the device, the device choosing the pixelwise gain factors from a table assigned to the actual distance of the antiscatter grid from the focus. In this case, the device may be designed for the computational adaptation of the gain factors taken from the chosen table in the case of a difference between the actual distance and the distance on which the table is based.

By way of example, in the case of an antiscatter grid focused at a film-focus distance of 150 cm, correction tables are created with respect to the distances 170 cm, 190 cm and 130 cm, 110 cm, respectively. In order, then, to obtain an optimum amplification in the case of an actual distance which lies between these values, the gain factors which are taken from the nearest table and are to be processed can be adapted computationally, e.g. in a manner dependent on the difference "actual distance:table distance", etc.

Finally, the device may be designed for the amplification of the pixel signals only of those pixels whose signals—relative to the defocusing-dictated signal attenuation exclusively of the antiscatter grid without a transillumination object situated in the beam path—lie below a predetermined threshold value, it being possible for the threshold value to define a defocusing-dictated attenuation of 40% or less. It is also conceivable to design the device for the amplification of the signals to a predetermined threshold value which lies below 100% relative to the signal that has been corrected by way of the flat field correction which has been determined in the context of an earlier calibration. In this case, too, the threshold value may define a signal attenuation of 40% or less and may be adjustable like the abovementioned threshold value.

The antiscatter grid itself may be a linear grid having focused absorption lamellae. Moreover, a cell grid with a carrier structure defining the focused rectangular cells with a beam passage opening with an absorption coating applied to the inner sides of the carrier structure which face the beam passage openings may also be involved. Such cell grids are formed from radiation-transparent polymer resin e.g. in a rapid prototype method using the stereolithography technique.

BRIEF DESCRIPTION OF THE DRAWINGS

The present invention will become more fully understood from the detailed description of preferred embodiments given hereinbelow and the accompanying drawing, which is given by way of illustration only and thus are not limitative of the present invention, and wherein:

FIG. 4 shows a diagram for illustrating the calculated attenuation profile for different grid distances.

DETAILED DESCRIPTION OF THE PREFERRED EMBODIMENTS

Figure 1:
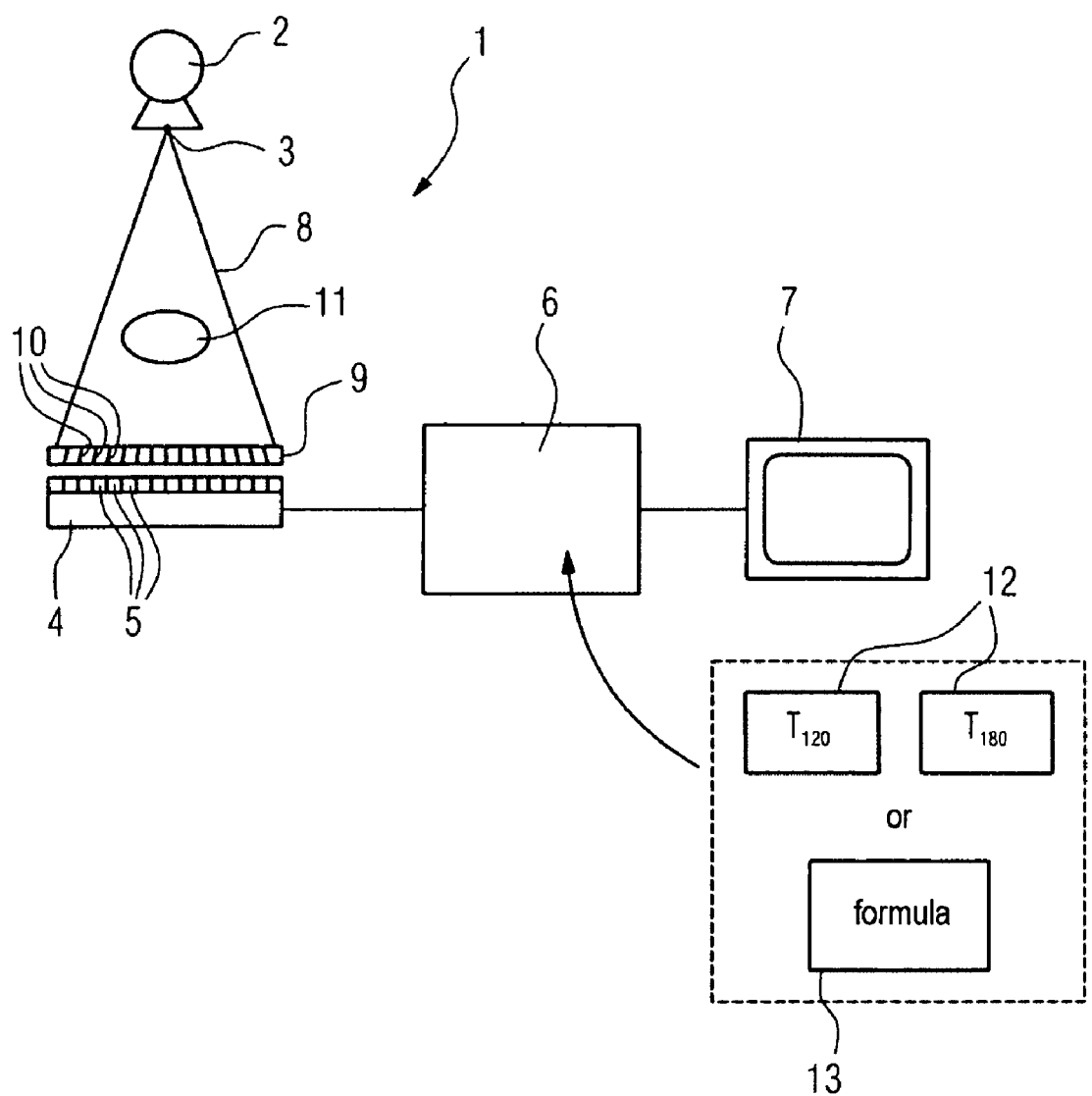
FIG. 1 shows an image recording apparatus according to an embodiment of the invention.

FIG. 1 shows, in the form of a schematic sketch, an apparatus 1 according to an embodiment of the invention for radiation image recording. This apparatus includes a radiation source 2 with a focus 3, a solid-state radiation detector 4 with a multiplicity of pixels 5 (e.g. approximately 3000× 3000 pixels), and also a device 6 assigned to the solid-state radiation detector 4 and serving for recording the pixel-generated signals, for processing the latter and for creating a radiation image that can be output at a monitor 7.

Arranged in the beam path 8, which clearly diverges proceeding from the focus, is an antiscatter grid 9, in the form of a linear grid in the exemplary embodiment shown, having a multiplicity of absorption lamellae 10 which are oriented with respect to the focus 3. A focused linear grid is thus involved. This focused antiscatter grid 9 absorbs scattered radiation which is scattered in the course of radiating through an object 11 situated in the beam path, since the antiscatter grid essentially transmits only the primary radiation that is not scattered, that is to say runs rectilinearly from the focus to the solid-state image detector 4.

The antiscatter grid 9 is focused and centered with respect to a specific distance of the focus 3 from the area of the pixel matrix 5. If the distance then changes, that is to say if the radiation source 2 is moved nearer to or away from the solid-state image detector 4, the antiscatter grid 9 is situated in a defocused position, that is to say the absorber lamellae are no longer oriented exactly with respect to the focus 3.

This has the effect that, with increasing defocusing, the proportion of primary radiation which is likewise absorbed undesirably by way of the absorber lamellae 10 increases. That is to say the imaging primary radiation dose that impinges on the pixel matrix 9 is consequently reduced. The dose decrease occurs to an intensified extent toward the edge and to a significantly lesser extent in the image center, since hardly anything changes at the absorber lamellae 10, which are essentially perpendicular in the image center region, with regard to their orientation with respect to the focus even in the defocused case.

Figure 2:
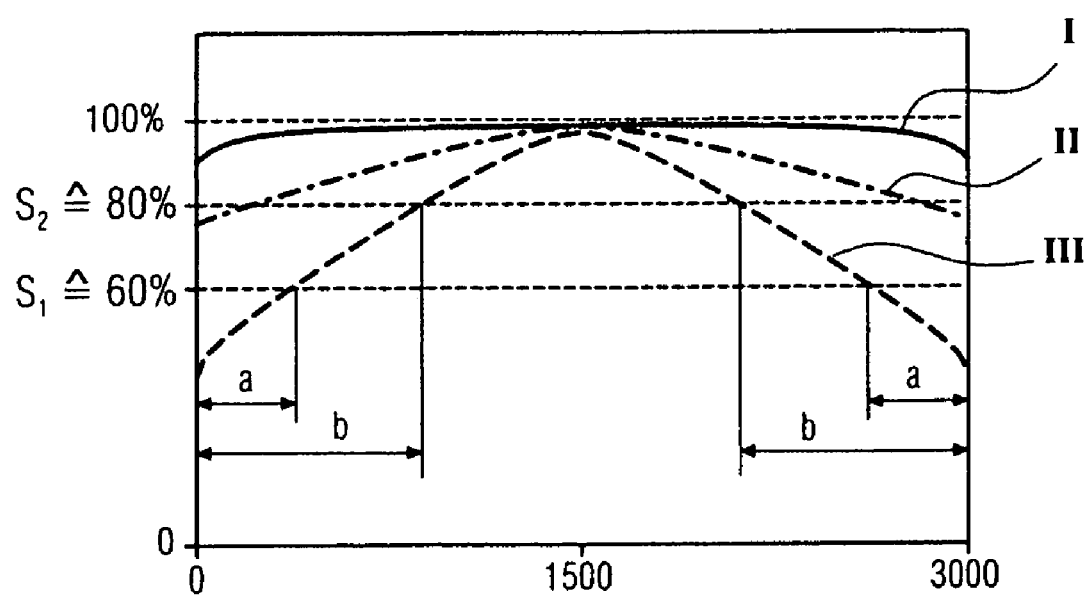
FIG. 2 shows a diagram for illustrating the signal profile and thus the attenuation over the pixel matrix in the case of a focused and defocused grid arrangement prior to an amplification of the pixel signals for the purpose of compensation.

FIG. 2 shows, in the form of a schematic diagram, the profile of the pixel signals over the area of the pixel matrix 5, 3000 pixels being provided here in a detector direction perpendicular to the course of the absorber lamellae of the grid. The local pixel position is plotted along the abscissa and the signal intensity is plotted along the ordinate. At 100%, no attenuation whatsoever is present.

The illustration shows three curves I, II and III. Curve I, which runs near to the 100% line, is the curve obtained if the antiscatter grid 9 is arranged exactly at the focusing distance. A minimal attenuation, governed by the square law of distance, results toward the edge. This intrinsic attenuation is compensated for by way of the device 6, to be precise computationally in the context of a global gain correction, where the divergence-dictated attenuation is compensated for.

For this purpose, firstly a first calibration is carried out, in the context of which only a copper filter is introduced into the beam path; the antiscatter grid 9 is not situated in the beam path. A signal curve is then recorded which exclusively shows the actually unattenuated signals and from which it is then possible to identify the dose decrease toward the edge. This dose decrease that results here is detected and compensated for in the context of the flat field correction.

Figure 3:
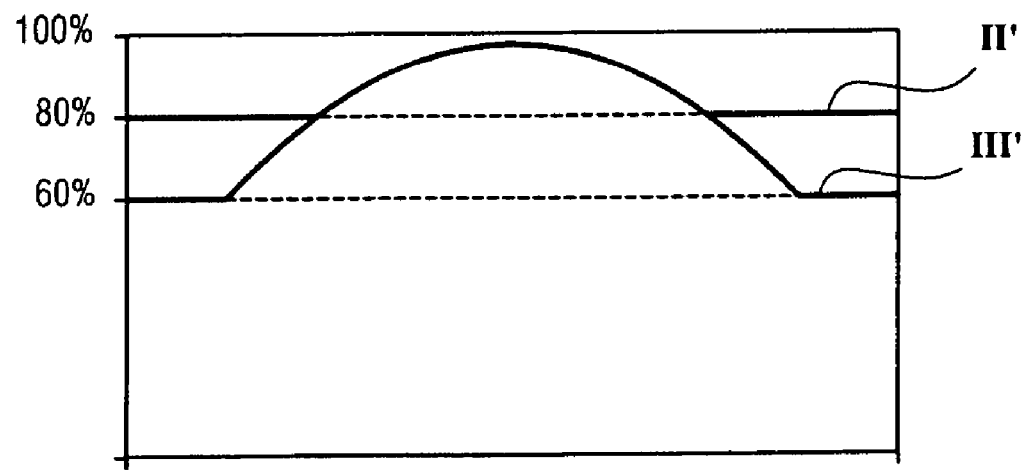
FIG. 3 shows the diagram from FIG. 2 after the signal elevation according to an embodiment of the invention.

FIGS. 2 and 3 show the curves in each case taking account of said flat field correction and specify only the focusing-dictated attenuation.

As described, curve I shows the signal profile after flat field correction with an antiscatter grid situated at the focusing distance. Curve II shows the signal profile if the distance of the focus 3 from the pixel matrix 5 is increased, that is to say the beam source 2 is moved away from the solid-state image detector 4. An ever-increasing attenuation can be seen there towards the edge regions, which attenuation, in the example shown, goes to somewhat less than 80% at the edge, in other words an attenuation of somewhat more than 20% is present at the edge. Proceeding from a focusing distance, to which the antiscatter grid 9 is focused, of e.g. 150 cm, curve II shows the exemplary case for a distance of 180 cm.

Curve III then shows the signal profile when the distance is shortened, that is to say if the beam source 2, proceeding from the focusing distance, is moved toward the solid-state image detector 4, e.g. to a distance of 115 cm. In this case, the dose decrease becomes significantly greater toward the edge since the clear width of the channels between the absorber lamellae 10 decreases to a significantly greater extent than when the distance is increased. The dose decrease amounts to up to approximately 50% in the edge regions.

The method according to an embodiment of the invention and also the apparatus according to an embodiment of the invention now permit this defocusing-dictated signal decrease to be compensated for as far as necessary. For this purpose—see FIG. 1—either different correction tables 12 are stored in the device 6, pixel-specific gain factors by which the signals of the exemplary curves II and III are amplified being stored in said correction tables. As an alternative to this, the device may also be designed for purely computational determination of the gain factors on the basis of the formula or the computation algorithm 13.

In the first-mentioned case, two correction tables which have been determined prior to the actual image recording in calibration recordings are present in the example shown. For this purpose, no object is situated in the beam path, but rather only the antiscatter grid 9 which is positioned at specific defocused distances. The focus distance from the pixel matrix was 120 cm in the case of the table $T_{120}$, and it was 180 cm in the case of the table $T_{180}$. For compensation purposes, that table which is nearest to the actual distance is then chosen, depending on the actual distance present. With regard to curve II, for compensation purposes, the table $T_{180}$ is chosen since the actual distance on which curve II is based corresponds to the correction table distance. In the case of curve III the table $T_{120}$ is chosen, the actual distance of 115 cm not corresponding to the correction table distance in this case.

The correction tables 12 store, for each pixel, the corresponding gain factor by which the pixel signal must be amplified in order to compensate the focusing-dictated signal attenuation to a desired value. Since the actual distance and the table distance correspond with respect to curve II, the gain factors of this table can be used directly. In the case of curve III and the table $T_{120}$, it is necessary for the gain factors of this table to be adapted computationally somewhat in order to be able to compensate for the difference between the actual distance and the table distance (115 cm to 120 cm).

Various method variants are conceivable with regard to the compensation, and these are illustrated with respect to curve III. Firstly, there is the possibility of amplifying only those pixel signals which lie below a specific threshold value or threshold value signal. A first threshold value signal $S_1$ corresponding to 60% signal or 40% attenuation was chosen in the example shown in accordance with FIG. 2.

As represented by the arrow a, only the pixel signals which lie below this threshold value $S_1$ are elevated in the context of the signal amplification. These signals can then be amplified to any desired value; FIG. 3 illustrates the case where the pixel signals are amplified to precisely the threshold value $S_1$, thus resulting in the curve III' shown in FIG. 3. Moreover, it is possible, of course, for these pixel signals that are to be amplified also to be elevated further, e.g. to a second threshold value. The latter may be chosen depending on the design of the apparatus; it may also be set on site, if appropriate.

Furthermore, FIG. 2 shows a second threshold value $S_2$, which corresponds to 80% signal strength or 20% attenuation in the example shown. The arrows b show that once again only those pixel signals which are attenuated by more than 20%, that is to say lie below $S_2$, are elevated. The resultant amplified curve II' is likewise illustrated in FIG. 3.

This amplification clearly permits sufficient compensation of the defocusing-dictated signal attenuation. If an object is then examined, a signal profile which deviates from the signal profiles without an examination object as shown in FIG. 2 and which is dependent on the object attenuation is obtained, of course, over the entire pixel matrix.

It is known from the correction tables, however, how the actual defocusing-dictated attenuation, which occurs in addition to the actual object attenuation and represents a disturbance component, affects the signals. The actual object image signals are then correspondingly elevated—insofar as they are to be elevated in accordance with the correction tables—so that ultimately only signals which essentially correspond to the actual object attenuation or reproduce the latter are used for the actual image generation.

The same correction may also be effected using the formula identified by 13 or said algorithm. This makes it possible, from the knowledge of the actual distance of the focus 3 from the pixel matrix 5 and also the knowledge of the relevant grid parameters, to determine the respective attenuation which occurs in defocusing-dictated fashion in the case of this actual distance and to determine the gain factors computationally without the need to store the correction tables already described.

The calculation of the attenuation profile over the detector area may be effected on the basis of the following formulae:

$$V1 = \frac{r*c*(f0-f1)}{f0*f1} \quad \text{(I)}$$

and $$V2 = \frac{r*c*(f2-f0)}{f2*f0} \quad \text{(II)}$$

The following are applicable in this case:
V1, V2=attenuation
r=shaft ratio
c=horizontal distance from the grid center in cm (location of the attenuation to be calculated).
f0=focusing distance in cm
f1, f2=actual distance of the grid from the focus in cm where V1 denotes the attenuation in the case where the distance is shortened below the focusing distance (f1<f0)

and V2 denotes the attenuation in the case where the distance is increased above the focusing distance (f2>f0).

On the basis of formulae (I) and (II), it is possible to calculate the profile of the attenuation in a manner dependent on the actual distance for each relevant point in the horizontal direction. Since the central ray defines the center, in the case of a detector having an edge length of 40 cm, the value c is chosen from the interval of 0 to +/−20 cm depending on a predetermined pitch, e.g. in 1 cm steps. The actual distance of the grid from the focus, which is detected by means of a suitable position sensor system, is detected as f1 and f2, respectively. Either the formula (I) or (II) is chosen depending on whether the actual distance is greater or less than f0.

If the actual attenuation at the point respectively considered is known, which attenuation has a linear profile in the case of calculation, it is possible to determine for each point considered whether or not it is to be amplified. By way of example, only those points or pixel signals which lie below the threshold value described, e.g. of 40% attenuation, are amplified. Depending on the configuration of the amplification mode, the signals to be elevated may then be amplified e.g. to a second threshold value, e.g. to the abovementioned 40%, so that overall specification-conforming image data are still present or a standard-conforming image can be generated. For this purpose, for each signal that is actually to be amplified, the relevant gain factor which enables the desired amplification is determined from the actual attenuation factor given. This is then processed together with the global gain factor.

FIG. 4 shows by way of example the attenuation profile for a few selected defocusing distances. The focusing distance was assumed to be 150 cm. The illustration additionally shows the attenuation profiles for the distances f2=160 cm, 170 cm and 180 cm. c, that is to say the distance from the central ray in mm, is plotted along the abscissa, only the values for f2 at 10 mm distances being illustrated by way of example. The attenuation V2 is specified along the ordinate.

The illustration shows only part of the overall attenuation profile in the "positive" c direction; the curves run with an opposite gradient for the other half of the diagram. The attenuation curves clearly have a linear profile. The attenuation curve at the focusing distance necessarily runs precisely on the abscissa, while the gradient increases as the defocusing distance increases. The same behavior results if the actual distance is shortened below the focusing distance.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for the compensation of image disturbances in the course of radiation image recording caused by defocusing of an antiscatter grid, arranged in the beam path between a beam source and a digital radiation image receiver and focused with respect to a specific distance from a focus of the beam source, the image disturbances being caused by a defocusing-dictated attenuation of primary radiation incident on the radiation image receiver, the digital radiation image receiver including radiation-sensitive pixels arranged in matrix form and a device for pixelwise amplification of the radiation-dependent signals, the method comprising:

amplifying at least some of the signals supplied by the digital radiation image receiver in pixelwise fashion, in a manner dependent on an actual distance of the antiscatter grid from the focus.

2. The method as claimed in claim 1, wherein pixel-related gain factors, by which the at least some of the signals are amplified, are determined computationally for the given actual distance of the antiscatter grid from the focus relative to the original focusing distance.

3. The method as claimed in claim 2, wherein only the pixel signals of those pixels whose signals, relative to the defocusing-dictated signal attenuation exclusively of the antiscatter grid, lie below a predetermined threshold value are amplified.

4. The method as claimed in claim 3, wherein the threshold value defines a defocusing-dictated attenuation of 40% or less.

5. The method as claimed in claim 2, wherein the signals are amplified by the gain factors to a predetermined threshold value.

6. The method as claimed in claim 5, wherein the threshold value defines a defocusing-dictated attenuation of 40% or less.

7. The method as claimed in claim 5, wherein the threshold value is adjustable.

8. The method as claimed in claim 1, wherein pixelwise gain factors, by which the at least some of the signals are amplified, are chosen from a table assigned to the actual distance of the antiscatter grid from the focus.

9. The method as claimed in claim 8, wherein, in the case of a difference between the actual distance and the distance on which the table is based, the gain factors are adapted computationally.

10. The method as claimed in claim 9, wherein only the pixel signals of those pixels whose signals, relative to the defocusing-dictated signal attenuation exclusively of the antiscatter grid, lie below a predetermined threshold value are amplified.

11. The method as claimed in claim 10, wherein the threshold value defines a defocusing-dictated attenuation of 40% or less.

12. The method as claimed in claim 8, wherein only the pixel signals of those pixels whose signals, relative to the defocusing-dictated signal attenuation exclusively of the antiscatter grid, lie below a predetermined threshold value are amplified.

13. The method as claimed in claim 12, wherein the threshold value defines a defocusing-dictated attenuation of 40% or less.

14. The method as claimed in claim 1, wherein only the pixel signals of those pixels whose signals, relative to the defocusing-dictated signal attenuation exclusively of the antiscatter grid, lie below a predetermined threshold value are amplified.

15. The method as claimed in claim 14, wherein the threshold value defines a defocusing-dictated attenuation of 40% or less.

16. The method as claimed in claim 14, wherein the threshold value is adjustable.

17. An apparatus for radiation image recording, comprising:
a beam source including a focus;
a digital radiation image receiver with radiation-sensitive pixels arranged in matrix form with an assigned device for the pixelwise amplification of the pixel signals; and
an antiscatter grid, arranged between the beam source and the digital radiation image receiver, the antiscatter grid being focused with respect to a specific distance from the focus of the beam source, wherein the assigned device is designed for compensation of image disturbances caused by a defocusing of the antiscatter grid, the image disturbances being caused by a defocusing-dictated attenuation of the primary radiation incident on the digital radiation image receiver, for pixelwise amplification of at least some of the signals supplied by the digital radiation image receiver in a manner dependent on the actual distance of the antiscatter grid from the focus.

18. The apparatus as claimed in claim 17, wherein the assigned device is designed for the computational determination of pixel-related gain factors, by which the at least some of the signals are amplified, for the given actual distance of the antiscatter grid from the focus relative to the original focusing distance.

19. The apparatus as claimed in claim 17, wherein at least one table with pixel-specific gain factors, assigned to at least one specific distance of the antiscatter grid from the focus and by which the at least some of the signals are amplified,, is stored in the assigned device, the assigned device choosing the pixelwise gain factors from a table assigned to the actual distance of the antiscatter grid from the focus.

20. The apparatus as claimed in claim 19, wherein the assigned device is designed for the computational adaptation of the gain factors taken from the chosen table in the case of a difference between the actual distance and the distance on which the table is based.

21. The apparatus as claimed in claim 17, wherein the assigned device is designed for the amplification of the pixel signals only of those pixels whose signals, relative to the defocusing-dictated signal attenuation exclusively of the antiscatter grid, lie below a predetermined threshold value.

22. The apparatus as claimed in claim 21, wherein the threshold value defines a defocusing-dictated attenuation of 40% or less.

23. The apparatus as claimed in claim 21, wherein the threshold value is adjustable.

24. The apparatus as claimed in claim 21, wherein the antiscatter grid is at least one of a linear grid with focused absorption lamellae and a cell grid with a carrier structure defining the focused rectangular cells with a beam passage opening with an absorption coating applied to the inner sides of the carrier structure which face the beam passage openings.

25. The apparatus as claimed in claims 17, wherein the assigned device is designed for the amplification of the signals to a predetermined threshold value.

26. The apparatus as claimed in claim 25, wherein the threshold value defines a defocusing-dictated attenuation of 40% or less.

27. The apparatus as claimed in claim 25, wherein the threshold value is adjustable.

28. The apparatus as claimed in claim 17, wherein the antiscatter grid is at least one of a linear grid with focused absorption lamellae and a cell grid with a carrier structure defining the focused rectangular cells with a beam passage opening with an absorption coating applied to the inner sides of the carrier structure which face the beam passage openings.

29. A method, comprising:

amplifying at least some of signals supplied in pixelwise fashion from a radiation image receiver, in a manner dependent on an actual distance of an antiscatter grid from a focus of a source of a beam; and compensating for image disturbances in a radiation image recording based upon the amplifying, the image disturbances being caused by defocusing of the antiscatter grid, arranged in a beam path and focused with respect to a specific distance from the focus of the source of the beam, and by a defocusing-dictated attenuation of primary radiation incident on the radiation image receiver.

30. An apparatus for radiation image recording, comprising:

means for generating a beam including a focus;

means for detecting the beam, including radiation-sensitive pixels arranged in matrix form, and including means for the pixelwise amplification of the pixel signals; and an antiscatter grid, arranged between the means for generating a beam and the means for detecting, the antiscatter grid being focused with respect to a specific distance from the focus of the means for generating the beam, wherein the means for the pixelwise amplification is designed for compensation of image disturbances caused by a defocusing of the antiscatter grid, the image disturbances being caused by a defocusing-dictated attenuation of primary radiation incident on the means for detecting, for pixelwise amplification of at least some of the signals supplied by the means for detecting in a manner dependent on the actual distance of the antiscatter grid from the focus.

* * * * *